United States Patent [19]

Wong et al.

[11] Patent Number: 5,652,139

[45] Date of Patent: Jul. 29, 1997

US005652139A

[54] DNA COMPRISING LAMB SECRETION SIGNAL SEQUENCE AND MATURE IGF-1 SEQUENCE

[75] Inventors: Edith Wong, Chesterfield, Mo.; Michael L. Bittner, Naperville, Ill.

[73] Assignee: Monsanto Company, St. Louis

[21] Appl. No.: 455,265

[22] Filed: May 31, 1995

Related U.S. Application Data

[62] Division of Ser. No. 704,489, May 23, 1991, which is a division of Ser. No. 522,399, May 10, 1990, Pat. No. 5,084,384, which is a continuation of Ser. No. 41,896, Apr. 23, 1987, abandoned.

[51] Int. Cl.$^6$ ............... C12N 1/21; C12N 15/18; C07K 14/65
[52] U.S. Cl. ............... 435/252.33; 435/69.7; 536/23.4; 536/23.51; 530/399
[58] Field of Search ............... 536/23.5, 23.51; 435/69.1, 69.8, 172.3, 252.33, 320.1; 530/303, 324, 399, 808; 935/47, 48

[56] References Cited

U.S. PATENT DOCUMENTS

| | | | |
|---|---|---|---|
| 4,336,336 | 6/1982 | Silhavy et al. | 435/68 |
| 4,411,994 | 10/1983 | Gilbert et al. | 435/69.7 |
| 4,689,406 | 8/1987 | Banks et al. | 435/68 |
| 4,738,921 | 4/1988 | Belagaje et al. | 435/68 |
| 4,757,013 | 7/1988 | Inouye et al. | 435/70 |
| 5,015,573 | 5/1991 | Yarranton et al. | 435/69.1 |

FOREIGN PATENT DOCUMENTS 0 105 521  4/1984  European Pat. Off. .

OTHER PUBLICATIONS

Ghrayeb et al., 1984, EMBOJ, 3:2437–2442.
Buell et al., 1985, Nucl. Acids. Res., 13:1923–1938.
Freudl et al., 1987, (Jan.), J. of Bacti., 169:66–71.
Nagahari et al., 1985, EMBOJ, 4:3589–3592.
Dunn et al., 1983, J. Mol. Biol., 166; pp. 504–505.
Brosius et al., 1985, Gene, 27:161–172.
Benson et al., 1984, Proc. Natl. Acad. Sci. USA, 81:3830–3834.
Nucleic Acids Research, vol. 14, pp. 7487–7500, (1986), Abrahmsen et al.
Nucleic Acids Research, vol. 12, pp. 5145–5164, (1984), Watson.
Nucleic Acids Research, vol. 11, pp. 1283–1294, (1983), Oshuye et al.
Wong et al. Gene 68: 193–203, 1988.
Hoffman et al. PNAS 82: 5107–5111, 1985.
Dunn et al. J. Mol. Biol. 166: 477–535, 1983.
Nilsson et al. Nuc. Acids Res. 13(4): 1151–1162, 1985.
Sjostrom et al. EMBO J. 6(3):823–831, 1987.

*Primary Examiner*—Vasu S. Jagannathan
*Assistant Examiner*—Christine Saoud
*Attorney, Agent, or Firm*—Gary M. Bond

[57] ABSTRACT

A method for bacterially producing IGF-I is disclosed in which Gram-negative bacteria are caused to express a gene consisting of a lamB or ompF signal sequence operatively joined to a DNA sequence encoding IGF-I and producing IGF-I which is secreted into the periplasmic space of the bacteria.

7 Claims, 4 Drawing Sheets

IGF-1
(1)+(2)

Bgl 2       Ava 2                                                        Sal 1
(1) TTTGAGATCTCCGGCTGGTCCAGAAACTTTGTGTGGTGCTGAATTGGTCGACGCTTTGCAATTCGTCTGTGGTgacagagg-
    aaactctagaggcgaccaggtctttgaaacacaccacgactaaccagctgcgaaacgTTAAGCAGAACACCACTGTCTCC - (2)

NH₂-GlyProGluThrLeuCysGlyAlaGluLeuValAspAlaLeuGlnPheValCysGlyAspArgGly tttctacttcaacaagccaactggttacgttctcttctcttctagaagagct
                                                          Xba1
(2) AAGATGAAGTTGTTCGGGTTGACCAATGCCAAGAAGAAGATCTTCTCGA PheTyrPheAsnLysProThrGlyTyrGlySerSerArg
                                               IGF-1
                                               (3)+(4)
                                                       Xba1                                Sal1
(3) TTCTTCTTCTAGAAGAGCTCCACAAACTGGTATCGTCGACGAGAATGTTGTTTCAGATCCTGTGACTTGAGAagattggaaa-
    aagaagaagatctttctcgagtgtttgaccatagcagctgctacaacaaagtctaGGACACTGAACTCTTCTAACCTTT-(4)

SerArgArgAlaProGlnThrGlyIleValAspGluCysCysPheArgSerCysAspLeuArgArgLeuGluMet tgtactgtgctccattgaagccagctaagtctgcttaaagcttagttt
                                                       Hind3
    ACATGACACGAGGTAACTTCGGTCGATTCAGACGAATTTCGAATCAAA  (4)

TyrCysAlaProLeuLysProAlaLysSerAla-COOH

*FIG. 1*

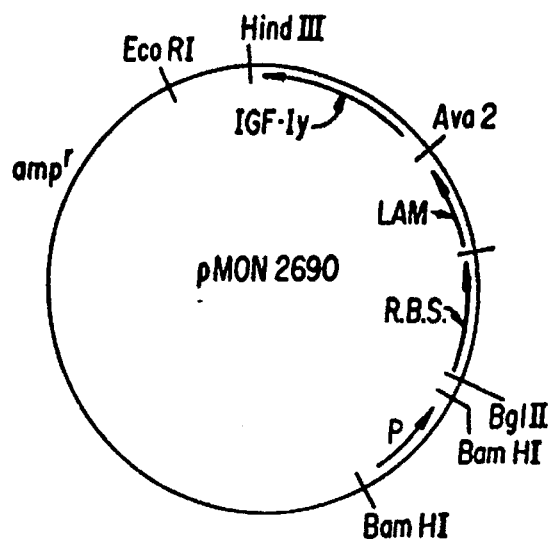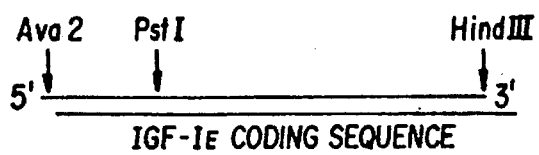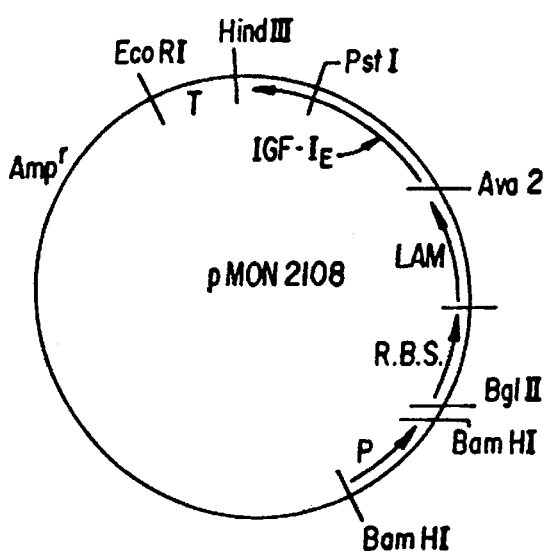
FIG. 2

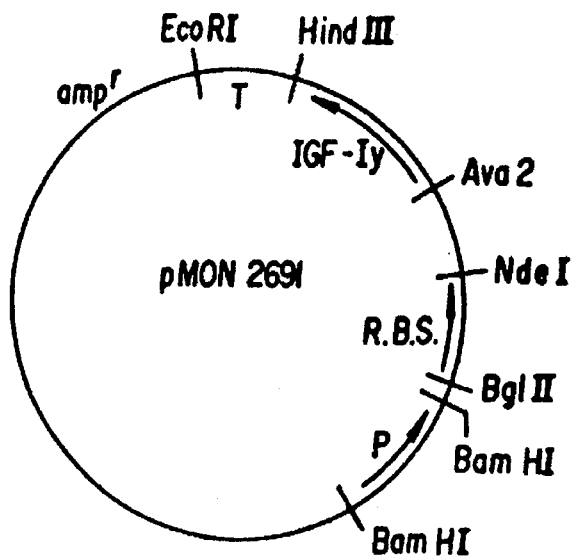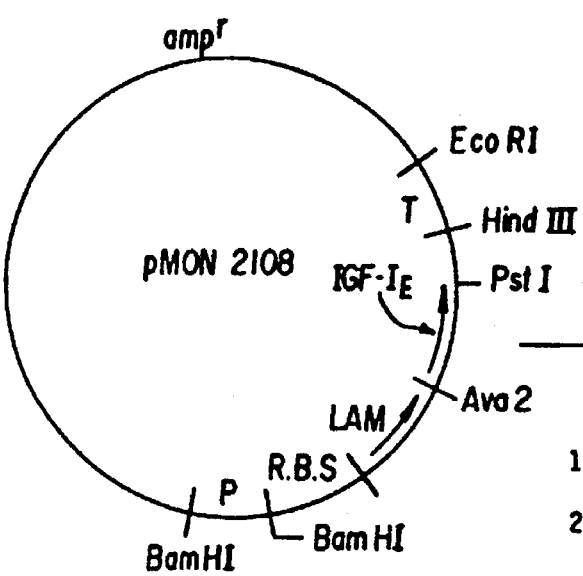
FIG. 3A

MATCH POINT (B) WITH POINT (A)
FIG. 3A SHEET 3
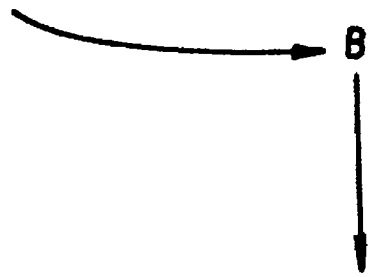
1. MIX: SYNTHETIC ompF CODING SEQUENCE WITH LARGE NdeI/EcoRI FRAGMENT FROM pMON2691 AND WITH IGF-$I_E$-T CONTAING Ava2/EcoRI FRAGMENT FROM pMON2108 IN THE PRESENCE OF T4 DNA LIGASE.
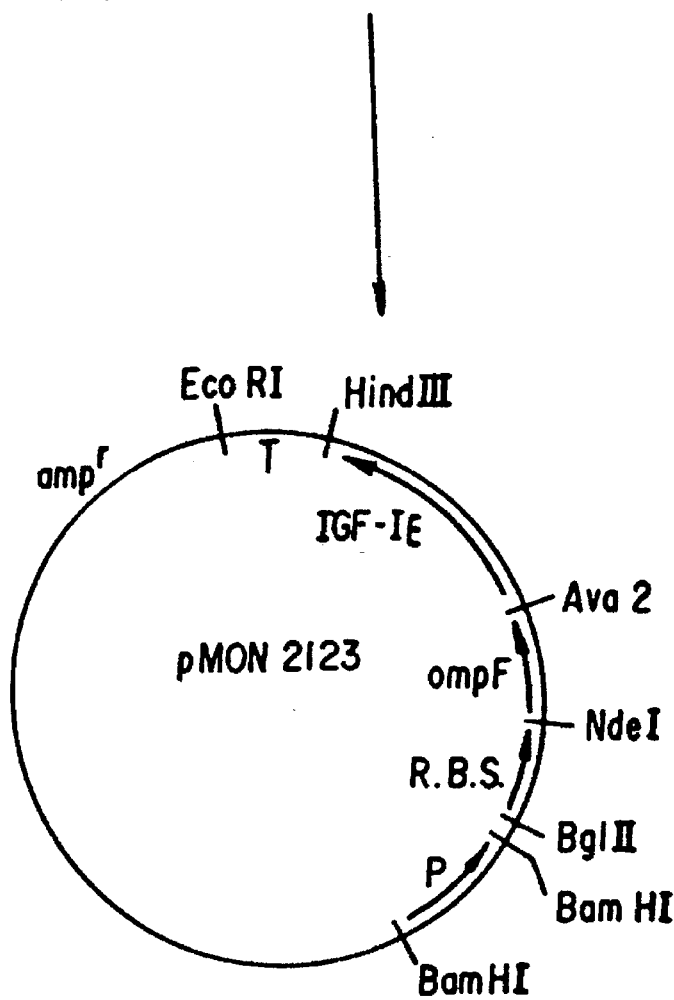
FIG. 3B

DNA COMPRISING LAMB SECRETION SIGNAL SEQUENCE AND MATURE IGF-1 SEQUENCE

This application is a divisional of U.S. Ser. No. 07/704, 489 filed May 23, 1991, now pending which is a divisional of U.S. Ser. No. 07/522,399 filed May 10, 1990, now issued as U.S. Pat. No. 5,084,384 which is a continuation of U.S. Ser. No. 07/041,896, filed Apr. 23, 1987, now abandoned.

TECHNICAL FIELD

The present invention is directed to methods and compositions for producing insulin-like growth factor (IGF) in Gram-negative bacteria. Such methods and compositions provide for the secretion of IGF by recombinant Gram-negative bacterial cells. In one preferred aspect, the IGF is secreted into the periplasmic space as a mature protein.

BACKGROUND OF THE INVENTION

Insulin-like growth factors (IGF's) have been isolated from various animal species and are believed to be active growth promoting molecules that mediate the anabolic effects of such hormones as growth hormone and placental lactogen. To date, several classes of IGF's have been identified. These include insulin-like growth factor-I (somatomedin C), insulin-like growth factor-II, Somatomedin A and a mixture of peptides called "multiplication-stimulating activity." This heterologous group of peptides exhibit important growth-promoting effects in vitro (Daugha-day, 1977; Clemmons and Van Wyk, 1981) and in vivo (Van Baul-Offers and Van de Brande, 1980; Schoenle, 1982).

Insulin-like growth factor-I (IGF-I) is a 70 amino acid basic protein (Rinderknecht and Humbel, 1978; Rubin et al., 1982) which has been demonstrated to play a fundamental role in postnatal mammalian growth as a major mediator of growth hormone action (Copeland et al., 1980; Zapf et al., 1981 and Schoenle et al., 1982). As such, IGF-I is useful in the treatment and/or potentiation of various growth related conditions.

The ability to obtain large quantities of IGF-I for commercial and therapeutic purposes has been hampered by the fact that the content of IGF-I in mammalian tissues is very low and, in contrast to insulin-like growth factor-II, no cultured mammalian cell lines have as yet been identified which elaborate significant quantities of IGF-I.

Natural sources of IGF-I thus far having proven inadequate to supply research and clinical needs, individuals and groups have turned to recombinant DNA techniques for the manufacture of IGF-I. Examples of such recombinant DNA methodologies can be found in European Patent Publication numbers 155,655 (published Sep. 25, 1985) which describes production of IGF-I as a cytoplasmic fusion protein; 135, 094 (published Mar. 12, 1985) which describes a process for producing IGF-I as a fusion protein in E. coli; 130,166 (published Jan. 2, 1985) which describes production of IGF-I as a cytoplasmic fusion protein in Staphylococcus aureus and production as a cytoplasmic protein containing an amino-terminal methionine in E. coli; 128,733 (published Dec. 19, 1984) which describes a process for producing IGF-I in the yeast Saccaromyces cerevisiae employing a yeast α-factor, a-factor or acid phosphatase signal sequence, and describes production of IGF-I as a cytoplasmic fusion protein; Nilsson, B. et al. (1985) which describes the cytoplasmic production of IGF-I as a Staphylococcal protein A—IGF-I fusion protein; and Buell et al. (1985) which describes intracellular production of IGF-I as a mature and fusion protein.

A process for producing IGF-I as a secreted protein in Gram-negative bacteria such as E. coli has not yet been disclosed. Such a process is desirable as current methods for production of IGF-I employing cytoplasmic production have required the use of fusion protein constructs to protect the mature IGF-I protein product from degradation by cytoplasmic proteases. (see European Patent Application publication number 135,094 supra and Buell et al. 1994). Fusion protein constructs have the disadvantage of requiring an additional production step consisting of release of mature IGF from the fusion protein. Such release is typically mediated by enzymatic or chemical means, which means can be harmful to the desired IGF-I protein and/or can require modifications in IGF-I protein structure (see e.g. European Patent Application publication number 135,094 supra). Secretion of mature IGF-I into the periplasm of such Gram-negative bacteria as E. coli would afford a compartmentalization of the IGF-I between the inner and outer cell membranes of the host cells thereby protecting the IGF-I from harmful cytoplasmic enzymes. Additionally, secretion into the periplasmic space allows for production of the IGF-I as a mature protein thereby eliminating the cumbersome and often costly release of mature protein from a fusion construct or otherwise undesirable amino terminal amino acids. Furthermore, production of IGF's in E. coli avoids the possibility of undesirable glycosylation which may occur when yeast host cells are employed.

Examples of various secretion systems described for use in E. coli include U.S. Pat. No. 4,336,336 (filed Jan. 12, 1979); European Pat. Application Publication Numbers 184, 169 (published Jun. 11, 1986), 177,343 (published Apr. 9, 1986) and 121,352 (published Oct. 10, 1984); Oka, T. et al. (1985); Gray, G. L. et al. (1985); Ghrayeb, J. et al. (1984) and Silhavy, T. et al. (1983). Briefly, these systems make use of the finding that a short (15–30) amino acid sequence present at the amino ($NH_2$-terminus of certain bacterial proteins, which proteins are normally exported by cells to noncytoplasmic locations, are useful in similarly exporting heterologous proteins to noncytoplasmic locations. These short amino acid sequences are commonly referred to as "signal sequences" as they signal the transport of proteins from the cytoplasm to noncytoplasmic locations. In Gram-negative bacteria, such noncytoplasmic locations include the inner membrane, periplasmic space, cell wall and outer membrane. At some point just prior to or during transport of proteins out of the cytoplasm, the signal sequence is typically removed by peptide cleavage thereby leaving a mature protein at the desired noncytoplasmic location. Site-specific removal of the signal sequence, also referred to herein as accurate processing of the signal sequence, is a preferred event if the correct protein is to be delivered to the desired noncytoplasmic location.

Attempts to employ such previously described signal sequences and secretion systems for delivery of heterologous proteins into the E. coli periplasmic space have, however, not always been successful. (see Kadonaga, J. et al., 1984; Ohsue, K. et al., 1983). Such results indicate that further studies are needed to clarify the secretion mechanism before secretion of heterologous proteins in such Gram-negative bacteria as E. coli can become a predictable phenomenon. The term "heterologous protein" is herein understood to mean a protein at least a portion of which is not normally encoded within the chromosomal DNA of a given host cell. Examples of heterologous proteins include hybrid or fusion proteins comprising a bacterial portion and a eucaryotic portion, eucaryotic proteins being produced in procaryotic hosts, and the like.

SUMMARY OF THE INVENTION

The present invention is directed to methods and compositions for producing insulin-like growth factor-I (IGF-I) in Gram-negative bacteria whereby the IGF-I so produced is secreted into the periplasmic space of the bacteria.

In one embodiment of the present invention, the methods comprise causing expression of a gene in Gram-negative bacteria, wherein the gene comprises a DNA sequence encoding a major outer membrane protein signal sequence operatively joined to a DNA sequence encoding IGF-I, so that the IGF-I produced within the bacteria is secreted into the periplasmic space thereof. It has been discovered that the lamB and ompF signal sequences provide for a site-specific release of the signal sequence from the IGF-I protein so that the IGF-I protein can be released into and accumulate at relatively high levels in the periplasmic space of selected bacteria.

Also provided are various synthetic DNA sequences and transformed bacteria useful in practicing the novel methods as provided herein.

BRIEF DESCRIPTION OF THE FIGURES

In the following diagrammatic representation, the directional arrows represent the 5' to 3' orientation of a DNA coding sequence(s) (e.g. direction of transcription of a DNA coding sequence), "amp$^r$" denotes an ampicillin resistance gene, "P" denotes a promoter sequence operable in $E.$ $coli$, "R.B.S." denotes a ribosome binding site, "LAM" denotes a DNA sequence coding for a lamB signal sequence, "IGF-I$_Y$" denotes an IGF-I coding sequence comprising yeast preferred codons, "IGF-I$_E$" denotes a IGF-I coding sequence comprising $E.$ $coli$ preferred codons and "T" denotes a transcription termination sequence. Relevant restriction endonuclease sites are also shown. The DNA regions marked as described above are for diagrammatic purposes only and are not drawn to scale unless otherwise noted.

FIG. 1 depicts the construction of a synthetic double-stranded (ds) IGF-I DNA coding sequence. The four chemically synthesized oligonucleotide portions of the synthetic coding sequence are shown in capital letters and are numbered IGF-1 (1) (2) (3) & (4). Regions of overlap between the chemically synthesized oligomers are denoted by a solid line (−) between complementary nucleotides. The lower case letters denote enzymatically generated oligonucleotides. The amino acid sequence of the IGF-I peptide encoded in the synthetic dsDNA sequence is shown in an amino (N$_2$)-terminal to carboxyl (COOH)-terminal orientation.

FIG. 2 depicts the construction of pMON2108, an IGF-I expression vector comprising a DNA sequence coding for a lamB signal sequence operatively joined to an IGF-I coding sequence consisting of $E.$ $coli$ preferred codons.

FIG. 3A & B depict the construction of pMON2123, an IGF-I expression vector comprising a DNA sequence coding for an ompF signal sequence operatively joined to an IGF-I coding sequence consisting of $E.$ $coli$ preferred codons. "ompF" denotes the DNA coding sequence for the ompF signal sequence.

DETAILED DESCRIPTION OF THE INVENTION

As used herein, the symbols representing amino acids (i.e. Ala for alanine) and nucleotides (e.g. C,G,A,T,) are those conventionally employed (Lehninger, 1976).

The present invention provides a means for producing IGF-I in Gram-negative bacteria whereby the IGF-I so produced is secreted into the periplasmic space of the bacteria. The discovery of such a means is significant as it allows for the direct production of mature IGF-I free from any undesirable amino acids and allows for an accumulation of mature protein in a readily accessible site and at a site free from harmful cytoplasmic proteases. The term "mature" when used to characterize an IGF-I protein means a protein essentially free from any extraneous NH$_2$- or carboxyl (COOH)-terminal amino acids. An example of such a protein is one having the primary amino acid sequence as shown in FIG. 1. Furthermore, the processes and compositions of the present invention provide for production of IGF-I at relatively high levels (e.g. 4 to 8% of total cellular protein produced).

The signal sequences which were discovered to effect high level production and secretion of accurately processed IGF-I are two signal sequences of major $E.$ $coli$ outer membrane proteins. $E.$ $coli$ possess a plurality of major outer membrane proteins including, but not limited to, lamB, ompF, ompA, ompC and phoE. These proteins are all synthesized in the cytoplasm and transported to their outer membrane location. As such, these proteins all contain a signal sequence which is processed either before or during transport of the mature outer membrane protein from the cytoplasm to its noncytoplasmic location. As described more fully hereinafter, the signal sequences of the $E.$ $coli$ lamB and ompF proteins provide accurate processing of the signal sequence when operatively joined to IGF-I peptides. The lamB and ompF signal sequences also provide for secretion and accumulation of mature IGF-I in the periplasmic space of the Gram-negative (e.g. $E.$ $coli$) host cells and allow high level production of IGF-I by the transformed host. Based upon these findings, it is believed that other $E.$ $coli$ major outer membrane protein signal sequences can effect the secretion and accumulation of mature IGF-I in the periplasmic space.

It is known that all Gram-negative bacteria possesses an outer membrane. It is also known that most members of the family Enterobacteriaceae possess a maltose-inducible outer membrane protein homologous to the lamB protein of $E.$ $coli$ (see Bloch and Desaymard, 1985, incorporated herein by reference hereto). Thus, it is expected that at least some of the lamB signal sequences of other Enterobacteriaceae, such as Shigella, Enterobacter, and Klebsiella, can effect secretion of mature IGF-I into the periplasmic space particularly when the host cell belongs to the same or sufficiently homologous genus and species from which the outer membrane protein signal sequence was derived.

In one embodiment of the present invention employing an $E.$ $coli$ expression system described more fully hereinafter, the preferred lamB signal sequence comprised the following amino acid sequence:

```
              1                           10
NH2-Met-Met-Ile-Thr-Leu-Arg-Lys-Leu-Pro-Leu-Ala-Val-
                           20
    Ala-Val-Ala-Ala-Gly-Val-Met-Ser-Ala-Gln-Ala-Met-Ala-
    COOH;
``` and the preferred ompF signal sequence comprised the following amino acid sequence:

```
              1                           10
NH2-Met-Met-Lys-Arg-Asn-Ile-Leu-Ala-Val-Ile-Val-Pro-
```

-continued

Ala–Leu–Leu–Val–Ala–Gly–Thr–Ala–Asn–Ala–COOH.

Significantly, several other *E. coli* non-outer membrane protein signal sequences reported to effectively secrete *E. coli* and/or heterologous proteins into the periplasmic space were found to be unable to secrete accurately processed mature IGF-I into the periplasmic space and/or did so at levels significantly lower than the lamB or ompF systems. The failure of such other signal sequences to effect secretion of mature IGF-I into the periplasmic space to a significant degree is in keeping with prior reports of inabilities to predict the secretion efficacy of a given signal sequence for a given peptide.

In order to effect secretion of mature IGF-I using the lamB or ompF signal sequences, the signal sequences are operatively joined to the IGF-I peptide. For the lamB signal, such operative joining can be achieved by at least two distinct means. In one preferred means, the lamB signal sequence was directly joined (e.g. by peptide bonding) at its carboxyl-terminus to the amino-terminus of the IGF-I peptide. The lamB signal sequence and IGF-I peptide are thus contiguous with one another. Alternatively, the lamB signal sequence is operatively joined to the IGF-I peptide by creating a hybrid (heterologous) protein containing sequentially from the $NH_2$-terminus a lamB signal sequence, at least 39 to 43 of the $NH_2$-terminal amino acids of the *E. coli* lamB protein and an IGF-I peptide (see Silhavy, et al., 1977; Silhavy et al., 1976). The DNA sequence of the *E. coli* lamB protein has been published by Clement and Hofnung (1981) which publication is hereby incorporated herein by reference hereto. In a preferred embodiment, the $NH_2$-terminal portion of the mature lamB protein comprised the following amino acid sequence:

$NH_2$—Val—Asp—Phe—His—Gly—Tyr—Ala—Arg—Ser—Gly—Ile—Gly—Trp—Thr—

Gly—Ser—Gly—Gly—Glu—Gln—Gln—Cys—Phe—Gln—Thr—Thr—Gly—Ala—

Gln—Ser—Lys—Tyr—Arg—Leu—Gly—Asn—Glu—Cys—Glu—COOH.

In both instances, when employing the expression vectors and systems hereinafter described, mature IGF-I is successfully secreted into the periplasmic space of the Gram-negative host cell and is produced at high levels (e.g. 4–8% of total cellular protein produced).

In one embodiment of the present invention, operative joining of an ompF signal sequence to an IGF-I peptide is achieved by similarly constructing (e.g. producing) heterologous proteins consisting of an ompF signal sequence at the $NH_2$-terminus and an IGF-I peptide at the COOH-terminus so that the signal sequence and IGF-I peptide are contiguous with one another. These heterologous proteins successfully secreted mature IGF-I into the periplasmic space of the Gram-negative host cells. Furthermore, the IGF-I so secreted is accumulated at levels similar to those achieved using a lamB signal sequence.

Having discovered that such major outer membrane protein signal sequences as the lamB and ompF signal sequences effect the secretion of mature IGF-I into the periplasmic space of such Gram-negative bacteria as *E. coli*, it is now possible to use conventional recombinant DNA techniques to produce the heterologous proteins described above (e.g. proteins consisting of a lamB or ompF signal sequence operatively joined to an IGF-I peptide).

In one embodiment of the present invention, production of heterologous proteins comprising a lamB or ompF signal sequence operatively joined to an IGF-I peptide is achieved as follows. A synthetic gene is constructed which contained the following components sequentially aligned in a 5' to 3' orientation: a promoter, a ribosome binding site, a translation start/signal codon contiguous with a DNA sequence encoding the heterologous protein sought to be produced and a translation stop codon. Such a synthetic gene can be constructed by conventional recombinant DNA techniques (see Maniatis et al., 1982) and by employing the methods and compositions set forth herein. The term "gene" refers to DNA sequences which provide for production of protein(s) encoded therein. The term "synthetic" is understood to mean a chemically and/or enzymatically generated nucleic acid sequence or molecule free from naturally occurring intervening or contiguous sequences. Also embraced in the term "synthetic" are chemically and/or enzymatically generated molecules or sequences which are combined with nucleic acid sequences or molecules with which they are not naturally found associated or combined. Examples of synthetic genes, molecules or sequences include, but are not limited to, nucleic acid sequences enzymatically or chemically released from a larger (e.g. naturally occurring) molecule and genomic DNA which has been modified by nucleic acid addition, deletion and/or rearrangement. The term "genome" or "genomic" as used herein means the total DNA (e.g. chromosomal and extrachromosomal) contained within a given cell.

In constructing a synthetic gene or genes which encode a heterologous protein comprising a lamB or ompF signal sequence operatively joined to an IGF-I peptide, any promoter capable of causing transcription in Gram-negative bacteria of such a gene or genes can be employed. Examples of such promoters are well known and available to those skilled in the art and include, without limitation, bacterial, viral and plasmid gene promoters (Rosenberg and Court, 1979). DNA molecules containing such promoter sequences can be isolated either by cloning the desired regions or, more conveniently, by chemically synthesizing them. A preferred promoter is the *E. coli* recA promoter, the sequence of which has been published (see Sancar & Rupp, 1979; and Sancar et al. 1980) and is furthermore contained on plasmid pMON2690 as a BamHI restriction fragment (see FIG. 2). *E. coli* carrying plasmid pMON2690 have been deposited with the American Type Culture Collection (Rockville, Md.) under accession number 67325.

Similarly, DNA sequences encoding the desired heterologous proteins which proteins can effect the secretion of IGF-I and preferably, mature IGF-I peptides into the periplasmic space, can also be chemically or enzymatically synthesized. The sequences of the lamB and ompF signal sequences have been published (Silhavy et al., 1983; Nagahari et al., 1985) as have the sequences of the lamB and ompF proteins (Inokuchi, K. et al., 1982, 1984; Silhavy, T. et al., 1983). Thus, DNA sequences encoding these proteins or any desired fragment thereof can be synthesized or isolated from appropriate gene or cDNA libraries by conventional methods. Thereafter, the synthetic DNA sequence encoding the desired lamB or ompF signal sequence can be operatively joined, by such means as ligase, to a DNA sequence encoding IGF-I.

The primary amino acid sequence of IGF-I has been published (Rinderknecht and Humbel, 1978) and is shown in FIG. 1. From the primary amino acid sequence, a plurality of DNA coding sequences can be constructed based upon the genetic code. Selection of the specific amino acid codons to be employed in generating an IGF-I DNA coding sequence is generally guided by such factors as determining a sequence which will optimize transcription, translation and, ultimately, the amount of protein produced. Selection of codons is thus, for example, guided by a desire to avoid potential secondary structure constraints, a preferred use of codons by the host cell (Fiers et al., 1976; Maruyama, T. et al., 1986; Sharp, P. et al., 1986; Bennetzen, J. and Hall, B., 1982; Gouy, M. and Gautier, C., 1982) and/or the need to provide for desired restriction endonuclease cleavage sites. An example of an IGF-I DNA coding sequence consisting of yeast preferred codons is shown in FIG. 1. An exemplary method for its construction is detailed in the examples below. Alternatively, an IGF-I coding sequence can be isolated from an appropriate cDNA library by conventional means.

As previously indicated, the synthetic genes of the present invention contained a ribosome binding site. In prokaryotic systems, a ribosome binding site such as a Shine-Dalgarno sequence (Shine and Dalgarno, 1974) has been demonstrated to be required for efficient translation of messenger RNA molecules. Recently, a novel ribosome binding site containing sequences from the gene 10 of bacteriophage T7 has been shown to be particularly effective in enhancing protein production. These novel bacteriophage T7 gene 10 sequences, herein referred to as "G10L sequences," are described more fully in U.S. patent application Ser. No. 005821 filed on Feb. 4, 1987 which is incorporated herein by reference hereto. The preferred synthetic genes of the present invention contained G10L sequences operatively joined to DNA sequences coding for the heterologous proteins of the present invention (e.g. proteins comprising a lamB or ompF signal sequence operatively joined to an IGF-I peptide).

In another preferred embodiment, the synthetic genes of the present invention further contain transcription termination sequences. Transcription termination sequences useful in the present invention include, without limitation, those found in bacteriophage and Gram-negative bacterial DNA (Holmes et al., 1983). A preferred transcription termination sequence derived from the gene 10 of bacteriophage T7 (Dunn and Studier, 1983) is described in U.S. patent application Ser. No. 005821 (supra).

Expression of the synthetic genes of the present invention and bacterial production of the heterologous proteins encoded therein is achieved as follows. The synthetic genes are inserted into expression vectors which vectors are then employed to transform such Gram-negative bacterial host cells as E. coli and Pseudomonas. Suitable host cells are identified by their respective abilities to provide for transport of IGF-I to the periplasm and accurate processing (e.g. removal) of the signal sequence in accordance with procedures described herein. An expression vector or vehicle is herein understood to comprise a DNA molecule such as a phage, plasmid or cosmid DNA capable of transforming a host cell, able to replicate genes inserted therein and facilitate expression of such genes in the transformed host cell. The term "transform" or "transformation" is herein understood to comprise any method for introducing exogenous DNA into the genome of a host cell. Such methods include, without limitation, transfection, transduction, infection and integration into chromosomal DNA. Any expression vector such as phage, plasmid or cosmid vectors known and/or available to those skilled in the art can be employed (see e.g. Maniatis et al., 1982). The preferred vectors included such pBR plasmid vectors as pBR327 (Soberon et al., 1980).

The insertion of the synthetic genes into expression vectors and/or construction or assembly of such genes therein can employ conventional methods known to those skilled in the art for insertion into or joining of nucleic acid molecules. Such methods include, without limitation, blunt-end or sticky-end ligation or chemical synthesis of desired coding or functional oligonucleotide sequences. FIG. 2 presents illustrations of two preferred expression vectors (denoted pMON2690 and pMON2108) carrying preferred synthetic genes of the present invention. These vectors contain a pBR327 origin of replication which permits autonomous replication of the vector in such host cells as E. coli and contains a drug resistance marker (amp$^r$) allowing selection of bacterial cells carrying (e.g. transformed with) the vectors.

Once such a vector is constructed, the essential components can be readily exchanged for alternative components by conventional recombinant DNA techniques. For example, by using the indicated restriction endonuclease sites additional and/or alternative DNA sequences can be inserted into the vectors by enzymatic or chemical linkage. Indeed, by employing the restriction endonuclease sites flanking that region of the expression vector containing DNA sequences encoding the ribosome binding site and lamB signal sequence, an alternate signal sequence, such as ompF, is inserted. By analogous means, alternate promoters, ribosome binding sites, and/or markers can be inserted into the expression vector.

In one embodiment, expression vectors containing a synthetic gene encoding a heterologous protein comprising a lamB or ompF signal sequence operatively joined to an IGF-I peptide were employed to transform Gram-negative host cells such as E. coli. Preferred host cells include E. coli strain SE6004 described by Liss et al. (1985) and Emr et al. (1981) and other such Gram-negative bacteria whose signal peptidase(s) is (are) able to accurately cleave the peptide bond joining the signal sequence and the heterologous peptide. E. coli strain SE6004 has been deposited with the American Type Culture Collection (ATCC) under accession number 53588.

The transformed host cells are then selected (Maniatis et al., 1982) and cultured under conditions which permit or cause expression of the synthetic gene. The resultant protein produced, comprising a lamB or ompF signal sequence operatively joined to an IGF-I peptide, provides for the efficient transport and accumulation of IGF-I peptides in the periplasmic space of the transformed host cell. Furthermore, the IGF-I so produced and accumulated is produced at high levels (at least 4–8% of total cellular protein), the signal sequences are accurately processed by the host cell and is biologically active.

Periplasmic proteins can then be selectively purified by such methods as lysozyme-EDTA (ethylenediaminetetraacetic acid) treatment (Oliver and Beckwith, 1982), spheroplasting (Neu et al., 1964), freeze-thaw treatments (European Patent Publication number 177, 343, published Apr. 9, 1986) or by osmotic shock (Oka et al., 1985). Insoluble proteins can be solubilized in such solvents as urea (e.g. 1.6 grams (wet weight) of cell pellet per milliliter of buffer comprising 2-6M urea) preferably at an alkaline pH and in the presence of a reducing agent, such as dithiothreitol. The solubilized proteins are then refolded by oxidization.

The levels of protein (e.g. IGF-I produced) can be determined by such conventional assays as Western immunoblotting, radioimmunoassay, protein staining of a protein gel and/or enzymatic activity. Examples of assays available for determination of IGF-I levels and bioactivity include, without limitation, radioimmunoassay (Copeland et al., 1980), radioreceptor assay (D'Ercole et al., 1976) and cell growth assays (Stiles et al., 1979; Kotts, C. E., 1984). By such means, it was determined that the IGF-I produced in accordance with the methods of the present invention was biologically active and represented from about 3 to 10% of the total produced by the transformed Gram-negative bacteria.

In some instances, a fraction of the proteins secreted into the periplasmic space leak through the host cell's outer membrane into the media. Indeed, in the secretion systems described herein, about 3 to 5% of the IGF-I protein produced can be purified from the growth medium. The percentage of protein which leaks into the culture medium can be increased, if desired, by employing such methods described in U.S. Pat. No. 4,595,658 to Zinder et al. Briefly, cells able to secrete the desired protein (e.g. IGF-I) into the periplasmic space are genetically altered by insertion of the f1 bacteriophage gene III into their genomes. Production of the gene III protein by Gram-negative bacteria such as E. coli causes perturbations in the outer membrane which, in turn, allows periplasmic proteins to leak out of the cell and into the media. Retrieval of proteins from the media can have advantages in such situations as when continuous culture conditions are being employed.

Microorganisms and Plasmids

The following microorganisms have been deposited with the American Type Culture Collection (ATCC), 12301 Parklawn Drive, Rockville, Md. 20852, U.S.A. in accordance with the Budapest Treaty:

| ATCC 53588 | E. coli SE6004 |
| ATCC 67325 | E. coli strain 294 (pMON2690) |

It should be understood that the availability of a deposit does not constitute a license to practice the subject invention in derogation of patent rights granted by governmental action. Furthermore, the present invention is not to be limited in scope by the microorganisms deposited since the deposited embodiments are intended only as specific illustrations of the invention.

EXAMPLES

Materials and Methods

All oligonucleotides were synthesized employing a 380A Applied Biosystems, Inc. DNA synthesizer in accordance with the procedure set forth by the manufacturer, Applied Biosystems, Inc., (Foster City, Calif.). Unless otherwise noted all specialty chemicals were obtained from Sigma (St. Louis, Mo.). Restriction enzymes and DNA modifying enzymes were purchased from New England Biolabs (Beverly, Mass.), New England Nuclear (Boston, Mass.) or Bethesda Research Laboratories (BRL) (Gaithersburg, Md.) and used in accordance with manufacturer's directions. T4 DNA ligase was purchased from Promega Biotec (Madison, Wis.) and used in accordance with manufacturer's specifications. $^{32}$P-labeled nucleotides and I$^{125}$-labeled protein A were purchased from Amersham (Arlington Heights, Ill.). E. coli strains SE2060 and SE6004 were obtained from Dr. Thomas Silhavy, Department of Molecular Biology, Princeton University, Princeton, N.J. 08544 and are described by Emr et al. (1981). E. coli strain SE6004 carrying a prlA4 mutation can be obtained from the ATCC (Rockville, Md.) under ATCC accession number 53588. E. coli strains W3110, 294 and JM101 can be obtained from the ATCC (Rockville, Md.) under ATCC accession numbers 27325, 31446 and 33876, respectively. All bacterial growth media components and antibiotics were obtained from either Sigma (St. Louis, Miss.) or Difco Laboratories (Detroit, Mich.). pBR327 vectors can be obtained from Pharmacia (Piscataway, N.J.).

The growth media for the E. coli and conditions for selection of bacterial cells carrying plasmids containing an ampicillin resistance (amp$^r$) marker were as described in Maniatis et al. (1982). When employed for protein expression, E. coli were grown in Luria broth (LB) or M9 minimal medium (Maniatis et al., 1982) supplemented with 100 µg/ml ampicillin. Transformation of E. coli host cells with recombinant vectors was performed as described in Maniatis et al. (1982).

Induction of transcription from the recA promoter was conducted briefly as follows. Overnight cultures of E. coli host cells carrying expression plasmids were diluted to 20–25 Klett units (measured with a Klett-Summerson meter using a green filter, Klett Mfg. Co., New York, N.Y.) in M9 minimal media supplemented with 0.25% (w/v) glucose and 1% (w/v) casamino acids and 0.25 µg/ml thiamine and grown to a cell density of 150–180 Klett units. The cells were then induced by adding nalidixic acid to the growth media at a final concentration of 50 µg/ml. Growth was continued for several hours at 37° C. with aliquots taken at 2 or 3 hours after induction for heterologous protein analysis. A high level of aeration was maintained throughout the growth in order to achieve maximal production of the desired gene product.

Periplasmic proteins produced in the E. coli host cells were obtained by an osmotic shock procedure essentially as described by Oka, T. et al. (1985). Specifically, cells from 30 ml of culture were pelleted and the supernatant collected. The supernatant was called the "media fraction." The pelleted cells were then resuspended in 5 ml of 20% (w/v) sucrose and 30 mM Tris pH 7.5. EDTA was then added to give a final EDTA concentration of $1 \times 10^{-3}$M. The resuspended cells were then incubated for 15 minutes at room temperature (about 20° C.) after which the cells were pelleted. The resulting supernatant was called the "sucrose fraction." The pelleted cells were resuspended in 3 ml of ice water (about 0°–4° C.) and shaken gently for 10 minutes in an ice bath and then pelleted. The resulting pellet and supernatant were called the "lysate" and "water wash," respectively. Typically, periplasmic proteins obtained by an osmotic shock procedure are found in the water wash fraction. The periplasmic IGF-I, however, was predominantly found in the sucrose fraction.

IGF-I was purified from the media as follows. Bacterial cells were removed by pelleting or passing the media through a 0.22µ membrane filter (Millipore, Inc.; Bedford, Mass.) after which the media was concentrated using a YM-3 membrane (Amacon Filter Co., Danvers, Mass.) and the protein then precipitated with 60% (w/v) ammonium sulfate. The precipitate was then pelleted, the pellet dissolved in 50 mM sodium formate (pH 4.2) and then desalted on a Sephadex G-25 column (Pharmacia, Piscataway, N.J.) after which the eluate was subjected to cation exchange chromatography on a mono S column (Pharmacia, Piscataway, N.J.) from which the IGF-I was eluted with a 0–1M sodium chloride gradient. The protein eluted at about 400 to 500 mM Nacl. The IGF-I containing fractions from the mono S column were then subjected to reverse phase high performance liquid chromatography on a Brownlee C8 RP300 Aquapore column (Brownlee Laboratories; Santa Clara, Calif.) from which the IGF-I was eluted with an acetonitrile-trifluoroacetic acid (TFA) gradient containing 0.1% (v/v) TFA. The IGF-I eluted at about 30% (v/v) acetonitrile. The recovered IGF-I was then stored at −20° to −80° C. as a lyophilized powder.

The levels of IGF-I produced by the bacterial host cells were determined by protein-specific assays such as protein staining (with Coomassie Brilliant Blue R250) of 15% (w/v) sodium dodecyl sulfate (SDS)-polyacrylamide gels (Laemmli, 1970) or by Western immunoblotting as described by Renart et al. (1979). Specifically, total protein produced within the host cell (cytoplasmic and periplasmic), protein secreted into the media and protein secreted only into the periplasmic space were determined as follows. Pelleted cells from 1 ml of culture were dissolved in SDS sample buffer as described by Laemmli (1970) to a final concentration of 1 Klett unit per µl. This sample represented the total protein produced within the host cell. The media fraction, sucrose fraction, water wash and lysate (all described above) were individually precipitated with trichloroacetic acid (TCA) and then redissolved in SDS sample buffer to a final concentration of 1 Klett unit/µl. All samples in SDS sample buffer were heated at 90° C. to 100° C. for 5 minutes prior to electrophoresis in 15% (w/v) SDS polyacrylamide gels (Laemmli, 1970). The Coomassie Brilliant Blue protein-stained gels were scanned by a Joyce Loeble chromoscan 3 scanning densitometer (Joyce Loeble, Inc., New Castle, Great Britain).

IGF-I specific antibody was prepared in accordance with the method of Vaitukaitis, J. L. (1981). Briefly, female New Zealand white rabbits were immunized intradermally with about 100 µg of IGF-I in Freund's Complete Adjuvant. The rabbits received intradermal booster injections of about 100 µg of IGF-I in Freund's Complete Adjuvant at 4 and 8 weeks.

Amino acid sequence analysis of bacterially produced heterologous proteins was performed using an Applied Biosystems, Inc. (Foster City, Calif.) Model 470A gas phase protein sequencer according to the methods described by Hunkapiller et al. (1983). The respective phenylthiodantoin (PTH)-amino acid derivatives were identified by reverse phase high performance liquid chromatography in an on-line fashion employing an Applied Biosystems, Inc. (Foster City, Calif.) Model 120A PTH Analyzer fitted with a Brownlee 2.1 mm inner diameter PTH-C18 column.

The bioactivity of IGF-I peptides isolated from the periplasmic space of recombinant gram negative bacteria was established by the rat L6 myoblast proliferation assay described by Kotts, C. E. (1984) and U.S. patent application Serial No. 777,117 which is incorporated herein by reference hereto. Specifically, IGF-I contained within the sucrose fraction following osmotic shock isolation was compared to a commercial preparation of human IGF-I obtained from Amgen, Inc. (Thousand Oaks, Calif., Lot 407) for demonstrable physiological activity in that assay. In order to minimize or eliminate any effects of sucrose in the L6 myoblast proliferation assay, the sucrose fraction samples (e.g. 2 ml of each sample) were first dialyzed versus one liter 44 mM NaHCO₃, pH 7.8, at 4° C., with three changes of dialysate over a three day period. The dialysis tubing had a molecular weight cut-off of 1000 kilodaltons. In all rat L6 myoblast proliferation assays conducted with the periplasmic IGF-I of the present invention, the IGF-I exhibited a statistically significant biological activity.

Radioimmunoassay analysis of both the dialyzed and undialyzed sucrose fraction was performed using a somatomedin C radioimmunoassay kit obtained from Nichols Institute (San Juan Capistrano, Calif.) in accordance with manufacturer's instructions.

EXAMPLE 1

This example describes the construction and assembly of the synthetic double-stranded IGF-I coding sequence shown in FIG. 1. In this Example 1, the coding portion of the sequence predominantly comprises yeast preferred codons as determined from the codon usage pattern in the yeast 3-phosphoglycerate kinase gene (Genbank Data base; see Bilofsky et al., 1986). Less preferred codons were also employed at some sites in the sequence in order to create or remove restriction sites and/or to minimize the possibility of competing secondary structure within the individual oligonucleotides. Oligonucleotides were synthesized as previously described and their respective concentrations determined using quantitative 5'-end labeling with $\gamma^{32}$P-ATP followed by separation of unincorporated $\gamma^{32}$P-ATP using ascending paper chromatography.

Construction and assembly of the synthetic IGF-I coding sequence was conducted in accordance with the methods described by Scarpulla et al. (1982); Rossi et al. (1982); and Adams & Galluppi (1986). Specifically, in order to produce the synthetic dsDNA sequence shown in FIG. 1, four partially overlapping synthetic oligonucleotides, designated IGF-I (1), (2), (3) and (4) and denoted by the capital letters, were synthesized. The oligonucleotides were annealed by mixing approximately equimolar quantities of each overlapping segment [e.g. IGF-I (1) was mixed with (2) and IGF-I (3) was mixed with (4)] and heating to 100° C. for about 2 min., cooling slowly (about 20 min.) to room temperature (about 20° C.) and incubating at room temperature for about 15 min. After annealing, the individual mixtures were diluted to a final concentration of 1 µM and incubated with about 2 units of *E. coli* DNA polymerase, Klenow fragment, in a buffer containing 10 mM Tris pH 8.0, 10 mM MgCl₂ and 0.25 mM of each deoxynucleoside triphosphate for 30 to 45 min. at room temperature. The reaction was stopped by heating to 70° C. for 10 min. and the DNA product then precipitated with ethanol. The dsDNA products which ranged from about 129 nucleotides for IGF-I (1) and (2) and about 128 nucleotides for IGF-I (3) and (4) were individually purified by electrophoresis on 8% (w/v) polyacrylamide gels containing 10% (v/v) glycerol. Multiple copies of each dsDNA product were then generated by cloning the products into a cloning vector. Useful cloning vectors include those described in Maniatis et al. (1982) and wherein the preferred cloning vectors include those vectors which facilitate DNA sequencing of the newly synthesized dsDNA product. Such preferred vectors include, but are not limited to pEMBL plasmids (Dente et al., 1983) and pTZ plasmids which contain a single-stranded origin of replication. Plasmids containing single-stranded origins of replication can be obtained from Pharmacia (Piscataway, N.J.). Once multiple copies of the dsDNA products were generated the products were excised from the cloning vectors and the IGF-I (1) and (2) dsDNA product ligated to the IGF-I (3) and (4) dsDNA product with T4 DNA ligase to form a dsDNA sequence coding for mature IGF-I.

EXAMPLE 2

This example describes the construction of various expression vehicles comprising synthetic IGF-I DNA coding sequences operatively joined to a secretion signal sequence. Specifically, expression vectors comprising a synthetic IGF-I DNA coding sequence consisting of either yeast or *E. coli* preferred codons operatively joined to a lamB or ompF signal sequence are described.

a. lamB

FIG. 2 presents diagrammatic representations of two expression plasmids, pMON2690 and pMON2108, which contain a DNA sequence encoding IGF-I operatively joined to a lamB signal sequence. The two plasmids are identical except that pMON2690 contains an IGF-I coding sequence comprising yeast preferred codons (denoted IGF-$I_y$) and pMON2108 contains an IGF-I DNA coding sequence comprising *E. coli* preferred codons (denoted IGF-$I_E$). *E. coli* strain 294 carrying plasmid pMON2690 has been deposited with the ATCC and given ATCC accession number 67325.

pMON2690 is a pBR327 plasmid having inserted therein the following DNA sequences in a 5' to 3' sequential orientation: a promoter (P), a ribosome binding site (R.B.S.), lamB signal sequence (LAM), IGF-I coding sequence (IGF-$I_y$) and a transcription termination sequence (T). Specifically, the promoter sequence comprised a recA promoter, the ribosome binding site comprised of a 100 base pair G10L sequence, the lamB signal sequence comprised a DNA sequence encoding the preferred lamB signal sequence previously described, the IGF-I coding sequence comprised the sequence shown in FIG. 1 and the transcription termination sequence comprised a bacteriophage T7 gene 10 transcription termination sequence. The DNA sequences contained within plasmid pMON2690 were either chemically and/or enzymatically synthesized, as described above, or isolated, by such recombinant DNA techniques a restriction cleavage (Maniatis et al., 1982), from available vectors containing the desired sequence(s). Once so generated, the desired DNA sequences were inserted into a pBR327 plasmid to achieve the described 5' to 3' sequence orientation.

As previously indicated, plasmid pMON2108 is identical to pMON2690 except that pMON2108 has an IGF-I DNA coding sequence comprising *E. coli* preferred codons (IGF-$I_E$) in lieu of yeast preferred codons. The IGF-$I_E$ DNA coding sequence contained within plasmid pMON2108 was chemically and enzymatically constructed in a manner analogous to the method described above for construction of the IGF-I DNA sequence comprising yeast preferred codons. The IGF-$I_E$ sequence was inserted into pMON2690 in place of the IGF-$I_y$ sequence to create pMON2108 as shown in FIG. 2. Specifically, pMON2690 was digested with restriction enzymes BglII and HindIII yielding two dsDNA fragments of pMON2690, one large and one small. These two dsDNA fragments were each isolated by electrophoresis in 0.8% (w/v) agarose gels (Maniatis et al., 1982) and thereafter eluted from the gels. The smaller dsDNA fragment containing the R.B.S., LAM and IGF-$I_y$ DNA sequences was then digested with restriction enzyme Ava2 and the about 210 base pair Ava2/HindIII fragment containing the IGF-$I_y$ sequence was then removed. The remaining Ava2/BglII fragment containing the R.B.S. and LAM sequences was then mixed, in the presence of T4 DNA ligase, with the large dsDNA fragment of pMON2690 generated and isolated as described above and a synthetic IGF-$I_E$ sequence containing an Ava2 sticky end at its 5'-end. The resultant plasmid was called pMON2108.

b. ompF

An expression plasmid containing the previously described ompF signal sequence in place of the lamB signal sequence in plasmid pMON2108 was constructed in a manner analogous to the method for pMON2108 construction described above (See FIGS. 3A and 3B). The resultant plasmid which contained, sequentially, a recA promoter, a G10L sequence, an ompF signal sequence, an IGF-$I_E$ coding sequence and a bacteriophage T7 gene 10 transcription termination sequence, was called pMON2123 and is shown in FIG. 3B.

Otherwise identical plasmids containing signal sequences derived from secreted non-outer membrane proteins in place of the lamB or ompF signal sequences were also constructed in accordance with the recombinant DNA techniques described herein.

EXAMPLE 3

*E. coli* strains SE6004, SE2060, W3110, JM101 and/or 294 were individually transformed (Maniatis et al., 1982) with one or each of the following expression vectors: pMON2690, pMON2108, pMON2123 or one of the otherwise identical plasmids containing a non-outer membrane signal sequence operably joined to an IGF-I DNA coding sequence. The IGF-I produced was then assayed for total IGF-I protein produced, accuracy of processing and biological activity in accordance with the previously described procedures. *E. coli* strain SE6004 was determined to be the preferred host for high level periplasmic production of accurately processed mature IGF-I. The lamB and ompF signal sequences were found to provide high levels (4–8% of total host protein produced) of accurately processed bioactive mature IGF-I in the periplasmic space. The non-outer membrane signal sequences failed to provide high levels of accurately processed mature IGF-I.

The foregoing examples illustrate preferred embodiments of the present invention and are not intended to limit the invention's scope in any way. While this invention has been described in relation to its preferred embodiments, various modifications thereof will be apparent to one skilled in the art from reading this application.

References

Adams, S. P., Galluppi, G. R. (1986) Medicinal Res. Reviews 6: 135.

Bennetzen, J. and Hall, B. (1982) J. Biol. Chem. 257: 3026–3031.

Bilofsky, H. S. et al. (1986) Nucleic Acids Res. 14: 1–4.

Block, M. A. and Desaymard, C. (1985) J. Bacteriol. 163: 106–110.

Buell, G. et al. (1984) Nucleic Acids Res. 13: 1923–1938.

Clement, J. M. and Hofnung, M. (1981) Cell 27: 507–514.

Clemmons, D. R. and Van Wyk, J. J. (1981) J. Cell Physiol. 106: 362–367.

Copeland, K. C., Underwood, L. E. and Van Wyk, J. J. (1980) J. Clin. Endocrinol. Metab. 50: 690–697.

Daughaday, W. H. (1977) Clin. Endocrin. Metab. 6: 117–135.

Dente, L., Cesareni, G. and Cortese, R. (1983) Nucleic Acids Res. 13: 1645–1655.

Dunn, J. J. and Studier, W. F. (1983) J. Mol. Biol. 166: 477–535.

Emr, S. E., Hanley-Way, S. and Silhavy, T. J. (1981) Cell 23: 79–88.

Fiers, et al. (1976) Nature 260: 500.

Ghrayeb, J., Kimuia, H., Takahara, M., Hsiung, H., Masui, Y. and Inouye, M. (1984) EMBO J. 3: 2437–2442.

Gouy, M. and Gautier, C. (1982) Nucleic Acids Res. 10: 7055–7074.

Gray, G. L., Baldridge, J. S., McKeown, K. S., Heyneker, H. L. and Chang, N. C. (1985) Gene 39: 247–254.

Holmes, M. W., Platt, T. and Rosenberg, M. (1983) Cell 32: 1029–1032.

Hunkapiller, M. W., Hewick, R. M., Dreyer, R. J. and good, L. E. (1983) Methods in Enzymology 91: 399–413.

Inokuchi, K., Matoh, N., Matsuyama, S. and Mizushima, S. (1982) Nucleic Acids Res. 10: 6957–6958.

Inokuchi, K. Furukawa, H., Nakamura, K. and Mizushima, S. (1984) J. Mol. Biol. 178: 653–668.

Kadonaga, J. et al. (February 1984) J. Biol. Chem. 259 (4): 2149–2154.

Kotts, C. E. Ph.D. Dissertation, Univ. of Minnesota, St. Paul, Minn.

Laemmli, U. K. (1970) Nature 227: 680–685.

Lehringer, A. L. (1976) *Biochemistry* 2nd ed., Worth Publishers, Inc., New York, N.Y. pp 72–75, 315–322.

Liss, L. R., Johnson, B. L. and Oliver, D. B. (1985) J. Bacteriol. 164: 925–928.

Maniatis, Fritsch and Sambrook, eds. (1982) *Molecular Cloning: A Laboratory Manual*, Cold Spring Harbor Laboratory, Cold Spring Harbor, N.Y.

Maruyama, T. et al. (1986) Nucleic Acids Res. 14 supplement: r151–r197.

Nagahari, K. et al., (1985) The EMBO Journal 4(USA): 3589–3592.

Neu, H., et al. (1964) Biochem. Biophys. Res. Comm. 17: 215.

Nilsson, B., Holmgren, E., Josephson, S., Gatenbeck, S., Philipson, L. and Uhlen, M. (1985) Nucleic Acids Res. 13: 1151–1162.

Ohsue, K., Nomura, M., Tanaka, S. Kubota, I., Nakazato, H., Shinagawa, H., Nakata, A. and Nogichi, T. (1983) Nucleic Acids Res. 11: 1284–1294.

Oka, T., Sakamoto, S., Miyoski, K., Fuwa, K., Yamasaki, M., Tamura, G. and Miyake, T. (1985) Proc. Nat'l. Acad. Sci., U.S.A. 82: 7212–7216.

Oliver, D. B. and Beckwith, J. (1982) Cell 30: 311–319.

Renart, J., Reiser, J. and Stark, G. R. (1979) Proc. Nat'l. Acad. Sci., U.S.A. 76: 3116–3120.

Rinderknecht, E. and Humbel, R. E. (1978) J. Biol. Chem. 253: 2769–2776.

Rosenberg and Court (1979) Ann. Rev. of Genet. 13: 319–353.

Rossi, J. J. et al. (1982) J. Biological Chem. 257: 9226.

Rubin, J. S. Muriz, I., Jacobs, J. W. Daughaday, W. H. and Bradshaw, R. A. (1982) Endocrinology 110: 734–740.

Sancar, A. and Rupp, W. D. (1979) Proc. Nat'l. Acad. Sci., U.S.A. 76: 3144–3148.

Sancar, A., Stachelek, C., Konigsberg, W. and Rupp, W. D. (1980) Proc. Nat'l. Acad. Sci., U.S.A. 77: 2611–2615.

Scarpulla, R. C., Narang, S. and Wu, R. (1982) Analytical Biochem. 121: 356.

Schoenle, E. Zapf, J., Humbel, R. E. and Froesch, E. R. (1982) Nature (London) 296: 252–253.

Sharp, P. et al., (1986) Nucleic Acids Res. 14: 5125–5143.

Shine, J. and Dalgarno (1974) Proc. Nat'l Acad. Sci., U.S.A. 71: 1342–1346.

Silhavy, T. et al. (1983) Microbiological Reviews 47 (3): 313–344.

Silhavy, T., Shuman, H., Beckwith, J. and Schwartz, M. (1977) Proc. Nat'l. Acad. Sci., U.S.A. 74: 5411–5415.

Silhavy, T., Casadaban, M., Shuman, H., Beckwith, J. (1976) Proc. Nat'l. Acad. Sci., U.S.A. 73: 3423–3427.

Soberon, X., Covarrubias, X. and Bolivar, F. (1980) Gene 9: 287–305.

Vaitukaitis, J. L. (1981) Methods in Enzymol. 73: 46–52.

Van Buul-Offers, S. and Van de Brande, J. L. (1980) in *Growth Hormone and Other Biologically Active Peptides* eds. Pecile, A. and Miller, E. E.; p. 103–122; Exerpta Medica, Amsterdam.

Zapf, J., Froesch, E. R. and Humbel, R. E., (1981) Current Topics Cell Reg. 19: 257–309.

We claim:

1. A DNA molecule comprising a first DNA sequence encoding lamB outer membrane protein secretion signal sequence free of any amino acids from mature lamB protein joined to a second DNA sequence encoding mature IGF-I protein free of extraneous amino terminus amino acids of the lamB protein, said lamB signal sequence consisting of Met-Met-Ile-Thr-Leu-Arg-Lys-Leu-Pro-Leu-Ala-Val-Ala-Val-Ala-Ala-Gly-Val-Met-Ser- Ala-Gln-Ala-Met-Ala, the 3' end of the first DNA sequence being contiguous with the 5' end of the second DNA sequence, and the joined sequences being effective upon expression in *E. coli* for producing secreted and accurately signal-sequence-processed extra-cytoplasmic mature IGF-I protein free of extraneous amino-terminus amino acids.

2. The DNA molecule of claim 1 wherein the DNA molecule comprises sequentially in the 5' to 3' direction a promoter, a ribosome binding site sequence, said first DNA sequence encoding lamB signal sequence, said second DNA sequence encoding mature IGF-I protein, and a transcription termination sequence.

3. An *E. coli* containing the DNA molecule of either of claims 1 or 2.

4. An *E. coli* of ATCC accession number 53588 and containing the DNA molecule of either of claims 1 or 2.

5. An *E. coli* containing a plasmid DNA molecule consisting of pMON 2108.

6. The DNA molecule of claim 2 wherein the promoter is a recA promoter.

7. The DNA molecule of claim 1, said mature IGF-I protein having the amino acid sequence set forth in FIG. 1.

* * * * *